(12) United States Patent
Cho et al.

(10) Patent No.: US 10,052,084 B2
(45) Date of Patent: Aug. 21, 2018

(54) ULTRASOUND DIAGNOSTIC APPARATUS AND METHOD OF OPERATING THE SAME

(71) Applicants: SAMSUNG ELECTRONICS CO., LTD., Suwon-si (KR); SAMSUNG MEDISON CO., LTD., Hongcheon-gun (KR)

(72) Inventors: Jeong Cho, Seoul (KR); Hyun Park, Hongcheon-gun (KR)

(73) Assignees: SAMSUNG ELECTRONICS CO., LTD., Suwon-si (KR); SAMSUNG MEDISON CO., LTD., Hongcheon-gun (KR)

(*) Notice: Subject to any disclaimer, the term of this patent is extended or adjusted under 35 U.S.C. 154(b) by 388 days.

(21) Appl. No.: 14/473,201

(22) Filed: Aug. 29, 2014

(65) Prior Publication Data
US 2015/0065881 A1    Mar. 5, 2015

(30) Foreign Application Priority Data

Aug. 29, 2013 (KR) .................. 10-2013-0103434

(51) Int. Cl.
*A61B 8/00* (2006.01)
*A61B 8/14* (2006.01)

(52) U.S. Cl.
CPC .............. *A61B 8/54* (2013.01); *A61B 8/429* (2013.01); *A61B 8/4444* (2013.01);
(Continued)

(58) Field of Classification Search
CPC ......... A61B 8/14; A61B 8/429; A61B 8/4444; A61B 8/4455; A61B 8/4472; A61B 8/467; A61B 8/54; A61B 8/56
See application file for complete search history.

(56) References Cited

U.S. PATENT DOCUMENTS 6,488,629 B1 * 12/2002 Saetre .................. A61B 8/08
600/443
9,218,452 B2    12/2015 Varna et al.
(Continued)

FOREIGN PATENT DOCUMENTS

CN        102525560 A        7/2012
JP        2012139491 A       7/2012
(Continued)

OTHER PUBLICATIONS

Notice of Allowance from the Korean Intellectual Property Office dated May 31, 2016 in a counterpart Korean Patent Application No. 10-2013-0103434.
(Continued)

*Primary Examiner* — Michael Rozanski
(74) *Attorney, Agent, or Firm* — Sughrue Mion, PLLC (57) ABSTRACT

An ultrasound diagnostic apparatus includes: a communicator including one of an antenna or a cable and configured to receive, using the one of the antenna or the cable, a signal from an ultrasound probe including a plurality of sensors, the ultrasound probe being external to the ultrasound diagnostic apparatus; and a controller including an electronic circuit configured to acquire a plurality of data sets corresponding to sensing results of the plurality of sensors from the signal, and perform a predetermined operation corresponding to a combination of the plurality of data sets, the plurality of data sets including information configured to synchronize timings when the plurality of data sets is acquired by the plurality of sensors, and the predetermined operation including transmitting a control signal corresponding to the combination of the plurality of data sets to the ultrasound probe.

15 Claims, 6 Drawing Sheets

(52) U.S. Cl.
CPC .......... *A61B 8/4455* (2013.01); *A61B 8/4472* (2013.01); *A61B 8/467* (2013.01); *A61B 8/56* (2013.01); *A61B 8/14* (2013.01)

(56) References Cited

U.S. PATENT DOCUMENTS

| | | | |
|---|---|---|---|
| 9,662,088 B2 * | 5/2017 | Pelissier | .................. A61B 8/06 |
| 2002/0065464 A1 | 5/2002 | Murphy et al. | |
| 2003/0139664 A1 | 7/2003 | Hunt et al. | |
| 2004/0015079 A1 * | 1/2004 | Berger | ................ G01S 7/52025 |
| | | | 600/437 |
| 2007/0161898 A1 * | 7/2007 | Hao | .................... G01S 15/8906 |
| | | | 600/443 |
| 2007/0161904 A1 | 7/2007 | Urbano | |
| 2008/0119737 A1 | 5/2008 | Urbano et al. | |
| 2008/0177181 A1 * | 7/2008 | Hastings | .............. A61B 5/0402 |
| | | | 600/440 |
| 2009/0318810 A1 | 12/2009 | Park et al. | |
| 2010/0168578 A1 * | 7/2010 | Garson, Jr. | .......... A61B 8/0858 |
| | | | 600/443 |
| 2013/0053697 A1 * | 2/2013 | Holl | ......... A61B 8/54 |
| | | | 600/459 |
| 2013/0178744 A1 | 7/2013 | Kierulf et al. | |
| 2013/0338501 A1 * | 12/2013 | Clingman | ............ A61B 5/0035 |
| | | | 600/440 |
| 2014/0128735 A1 * | 5/2014 | Newell | .................. A61B 8/543 |
| | | | 600/440 |
| 2014/0128738 A1 * | 5/2014 | White | .................... A61B 8/543 |
| | | | 600/447 |
| 2014/0171797 A1 * | 6/2014 | Hershey | .................. A61B 8/56 |
| | | | 600/437 |

FOREIGN PATENT DOCUMENTS

| | | |
|---|---|---|
| KR | 10-1024856 B1 | 3/2011 |
| KR | 10-1051601 B1 | 7/2011 |
| WO | 2008/146209 A1 | 12/2008 |

OTHER PUBLICATIONS

Office Action from the Korean Intellectual Property Office dated Oct. 29, 2015 in a counterpart Korean Patent Application No. 10-2013-0103434.

Communication dated Oct. 29, 2015, issued by the Korean Intellectual Property Office in counterpart Korean Patent Application No. 10-2013-0103434.

Communication dated Nov. 23, 2016, from the State Intellectual Property Office of People's Republic of China in counterpart Application No. 201410437981.6.

* cited by examiner

FIG. 6

ULTRASOUND DIAGNOSTIC APPARATUS AND METHOD OF OPERATING THE SAME

CROSS-REFERENCE TO RELATED APPLICATIONS

This application claims the benefit of Korean Patent Application No. 10-2013-0103434, filed on Aug. 29, 2013, in the Korean Intellectual Property Office, the disclosure of which is incorporated herein in its entirety by reference.

BACKGROUND

1. Field

One or more exemplary embodiments relate to an ultrasound diagnostic apparatus and a method of operating the same, and more particularly, to an ultrasound diagnostic apparatus which operates based on a combination of a plurality of data sets acquired by a plurality of sensors included in an ultrasound probe, and a method of operating the ultrasound diagnostic apparatus.

2. Description of the Related Art

Ultrasound systems irradiate an ultrasonic signal generated from a transducer of an ultrasound probe onto an internal part of an object and receive information of an echo signal reflected from the internal part of the object, thereby acquiring an image of the internal part of the object. In particular, ultrasound systems are used in medicine to observe the inside of an object, detect a foreign material, and assess an injury.

Ultrasound systems have higher stabilities than those of diagnostic apparatuses using X-rays, display an image in real time, and are safe because there is no exposure to radioactivity, and thus are widely used along with other medical image diagnostic apparatuses.

Ultrasound diagnostic apparatuses generate an ultrasound image by using ultrasonic image data acquired from an ultrasound probe, and display the generated ultrasound image on a screen to provide the ultrasound image to a user. The ultrasound diagnostic apparatuses may include a control panel for controlling an ultrasound system and setting various functions.

In general, a plurality of functional keys for receiving user input, and an input unit such as a keyboard, are mounted on a control panel of an ultrasound diagnostic apparatus. Therefore, in order for the user to control an ultrasound system including an ultrasound probe, various input units on the control panel have to be manipulated, thereby increasing inconvenience when using the ultrasound system. In particular, when the user performs a diagnosis of a patient by using the ultrasound probe, the user may be inconvenienced in manipulating the control panel that is spaced apart from the user and that takes a long time to manipulate.

Therefore, an ultrasound diagnostic apparatus enabling the user to control the ultrasound probe and the ultrasound system easily and conveniently is necessary.

SUMMARY

One or more exemplary embodiments include an ultrasound diagnostic apparatus capable of performing a predetermined operation based on a combination of a plurality of data sets acquired by a plurality of sensors included in an ultrasound probe so that a user may control the ultrasound diagnostic apparatus and the ultrasound probe rapidly and conveniently.

Additional aspects will be set forth in part in the description which follows and, in part, will be apparent from the description, or may be learned by practice of the presented exemplary embodiments.

According to one or more exemplary embodiments, there is provided an ultrasound diagnostic apparatus including: a communicator configured to receive a signal from an ultrasound probe comprising a plurality of sensors; and a controller configured to acquire a plurality of data sets corresponding to sensing results of the plurality of sensors from the signal, and perform a predetermined operation corresponding to a combination of the plurality of data sets.

The controller may be configured to perform the predetermined operation that includes at least one operation among operations of storing at least one data set of the plurality of data sets, displaying at least one data set of the plurality of data sets, and transmitting a control signal corresponding to the combination of the plurality of data sets to the ultrasound probe.

The ultrasound diagnostic apparatus may further include a storage configured to store the combination of the plurality of data sets and operations of the ultrasound diagnostic apparatus such that the combination of the plurality of data sets and the operations are mapped to each other, wherein the controller may be configured to search the operations stored in the storage for the predetermined operation corresponding to the combination of the plurality of data sets.

The controller may be configured to control the ultrasound diagnostic apparatus to store or display at least one of an acquired picture, a moving picture, and sound according to the sensing result of at least one of the plurality of sensors, based on the combination of the plurality of data sets.

The ultrasound diagnostic apparatus may be configured to transmit a control signal to the ultrasound probe, the control signal being configured to control the ultrasound probe to acquire ultrasound image data of an object by transmitting or receiving an ultrasound signal to or from the object, based on the combination of the plurality of data sets.

The signal may further include ultrasound image data of the object, and the controller may be configured to control the ultrasound diagnostic apparatus to store or display at least one data set of the plurality of data sets as information about the object with the ultrasound image data, based on the combination of the plurality of data sets.

The plurality of data sets may include information configured to synchronize timings when the plurality of data sets is acquired by the plurality of sensors.

The plurality of sensors may include at least one of a touch sensor, a proximity sensor, a microphone, and a camera.

According to another aspect of an exemplary embodiment, there is provided a method of operating an ultrasound diagnostic apparatus, the method including: receiving a signal from an ultrasound probe including a plurality of sensors; acquiring a plurality of data sets corresponding to sensing results of the plurality of sensors from the signal; and performing a predetermined operation corresponding to a combination of the plurality of data sets.

The performing of the predetermined operation may include performing the predetermined operation including at least one operation among operations of storing at least one data set of the plurality of data sets, displaying at least one of the plurality of data sets, and transmitting a control signal corresponding to the combination of the plurality of data sets to the ultrasound probe.

The method may further include storing the combination of the plurality of data sets and operations of the ultrasound diagnostic apparatus after mapping the combination of the plurality of data sets and the operations to each other, wherein the performing of the predetermined operation may include searching the operations for the predetermined operation corresponding to the combination of the plurality of data sets.

The performing of the predetermined operation may include storing or displaying at least one of an acquired picture, a moving picture, and sound according to the sensing result of at least one of the plurality of sensors, based on the combination of the plurality of data sets.

The performing of the predetermined operation may include transmitting a control signal to the ultrasound probe, the control signal being configured to control the ultrasound probe to acquire ultrasound image data of an object by transmitting or receiving an ultrasound signal to or from the object, based on the combination of the plurality of data sets.

The signal may further include ultrasound image data of the object, and the performing of the predetermined operation may include storing or displaying at least one data set of the plurality of data sets as information about the object with the ultrasound image data, based on the combination of the plurality of data sets.

The plurality of data sets may include information configured to synchronize timings when the plurality of data sets is acquired by the plurality of sensors.

The plurality of sensors may include at least one of a touch sensor, a proximity sensor, a microphone, and a camera.

According to another aspect of an exemplary embodiment, there is provided a non-transitory computer-readable recording medium having embodied thereon a program for executing a method of operating an ultrasound diagnostic apparatus in a computer, wherein the method may include: receiving a signal from an ultrasound probe including a plurality of sensors; acquiring a plurality of data sets corresponding to sensing results of the plurality of sensors from the signal; and performing a predetermined operation corresponding to a combination of the plurality of data sets.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the exemplary embodiments. Expressions such as "at least one of," when preceding a list of elements, modify the entire list of elements and do not modify the individual elements of the list.

Throughout the specification, when an element is referred to as being "connected" or "coupled" to another element, the element may be "directly connected or coupled" to the other element or "electrically connected or coupled" with intervening elements. When a part "includes" or "comprises" an element, unless there is a particular description contrary thereto, the part may further include other elements, and does not exclude the other elements.

Moreover, each of the terms such as " . . . unit" and "module" described in the specification denotes an element for performing at least one function or operation, and may be implemented in hardware, software or a combination of hardware and software.

The term "ultrasound image" used herein denotes an image of an object acquired by using an ultrasonic wave. Also, the term "object" used herein may be an organic substance or an inorganic substance indicated by the image. The object may include a part of a physical body. For example, an object may include an organ such as a liver, a heart, a womb, a brain, breasts, an abdomen, or the like, or a fetus, and may include a cross-sectional surface of the physical body.

Moreover, the term "user" used herein may refer to a medical expert, and may be a doctor, a nurse, a medical technologist, a sonographer, a medical image expert, or the like. However, the user is not limited thereto.

The exemplary embodiments will now be described more fully with reference to the accompanying drawings, in which exemplary embodiments are shown.

Figure 1A:
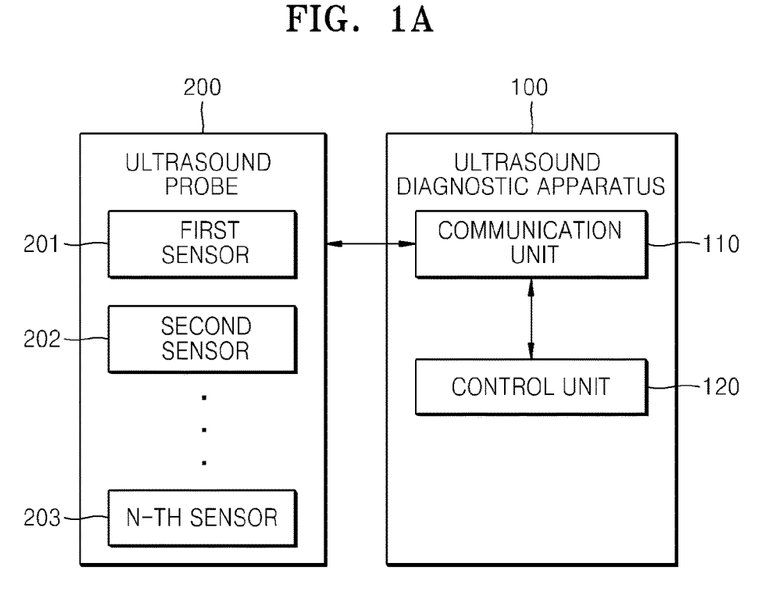
FIGS. 1A and 1B are block diagrams of an ultrasound diagnostic apparatus according to an exemplary embodiment.

FIG. 1A is a block diagram of an ultrasound diagnostic apparatus 100 according to an exemplary embodiment.

As shown in FIG. 1A, the ultrasound diagnostic apparatus 100 according to the present exemplary embodiment is connected to an ultrasound probe 200 through a wire or wirelessly to configure an ultrasound system.

The ultrasound probe 200 transmits an ultrasound signal to an object according to a control signal transmitted from the ultrasound diagnostic apparatus 100, receives an ultrasound signal reflected by the object (that is, an ultrasound echo signal), and forms a receiving signal. The ultrasound probe 200 focuses the receiving signal to form ultrasound image data, and transmits the ultrasound image data to the ultrasound diagnostic apparatus 100.

The ultrasound diagnostic apparatus 100 may form and display an ultrasound image based on the ultrasound image data transmitted from the ultrasound probe 200.

According to an exemplary embodiment, the ultrasound diagnostic apparatus 100 and a method of operating the ultrasound diagnostic apparatus 100 enable a user to control the ultrasound system rapidly and conveniently.

To achieve this, a method of receiving a control command from the user via various kinds of sensors provided in the ultrasound probe 200 is suggested as follows:

As shown in FIG. 1A, the ultrasound probe 200 according to the present exemplary embodiment includes a plurality of sensors. According to an exemplary embodiments, a "sensor" is a device capable of detecting various physical quantities, for example, sound, light, temperature, pressure, etc. The sensor may be included in a mechanical apparatus, although is not limited thereto.

For example, the ultrasound probe 200 may include a first sensor 201, a second sensor 202, . . . , and an Nth sensor 203. Here, the first, second, . . . , and Nth sensors 201, 202, and 203 may be different kinds of sensors that may sense different physical amounts, or the same kind of sensors that may sense a physical amount. Hereinafter, a case where the first, second, . . . , and Nth sensors 201, 202, and 203 are different kinds of sensors will be described as an example, for convenience of description.

The ultrasound probe 200 according to the present exemplary embodiment may acquire information about an object, information about a user, and information about a status of the ultrasound probe 200 via at least one of the first, second, . . . , and Nth sensors 201, 202, and 203. For example, at least one of the first, second, . . . , and Nth sensors 201, 202, and 203 may include a touch sensor, a proximity sensor, a microphone, a camera, or a combination sensor thereof.

In addition, the ultrasound diagnostic apparatus 100 of the present exemplary embodiment acquires a control command of the user from sensing results of the first, second, and Nth sensors 201, 202, and 203 so that the user may easily control the ultrasound system. Also, the ultrasound diagnostic apparatus 100 of the present exemplary embodiment may store the sensing results of the first, second, and Nth sensors 201, 202, and 203 with ultrasound image data of a patient, as patient information. Also, the ultrasound diagnostic apparatus 100 of the present exemplary embodiment acquires the sensing results of first, second, and Nth sensors 201, 202, and 203 as status information of the ultrasound probe 200, and displays the acquired status information of the ultrasound probe 200 so that the user may monitor the status of the ultrasound probe 200 in real-time.

As shown in FIG. 1A, the ultrasound diagnostic apparatus 100 according to an exemplary embodiment includes a communication unit 110 (e.g., communicator) and a control unit 120 (e.g., controller).

The communication unit 110 receives a signal from the ultrasound probe 200 including the first, second, and Nth sensors 201, 202, and 203.

The control unit 120 acquires a plurality of data sets corresponding respectively to the sensing results of the first, second, and Nth sensors 201, 202, and 203 from the signal transmitted from the communication unit 110. The control unit 120 performs a predetermined operation corresponding to a combination of the plurality of data sets.

According to an exemplary embodiment, the control unit 120 may determine which operation among a plurality of operations, for example, storing at least one of the plurality of data sets, displaying at least one of the plurality of data sets, and transmitting a control signal corresponding to the combination of the plurality of data sets to the ultrasound probe 200, is to be performed by the control command of the user, by combining the plurality of data sets.

Figure 1B:
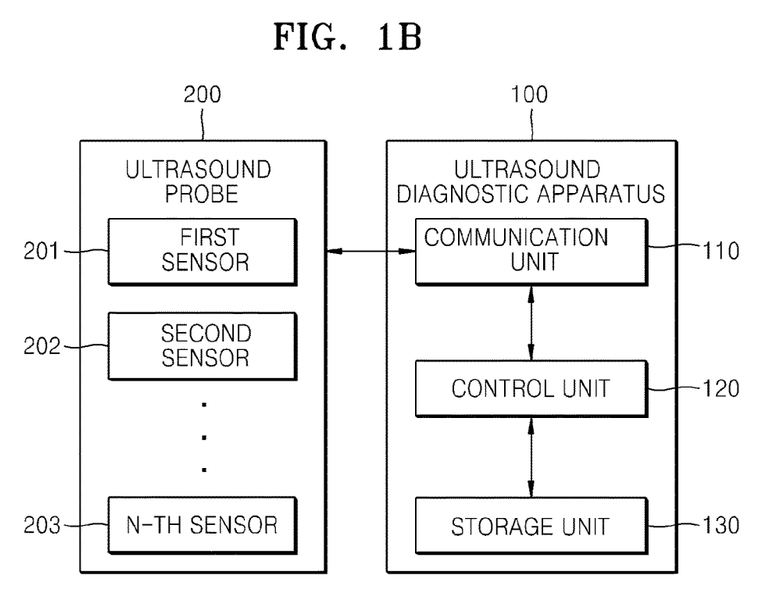

Also, as shown in FIG. 1B, the ultrasound diagnostic apparatus 100 of the present exemplary embodiment may further include a storage unit 130 (e.g., storage).

The storage unit 130 may store combinations of the plurality of data sets acquired by the first, second, and Nth sensors 201, 202, and 203 and operations that may be performed by the ultrasound diagnostic apparatus 100 after mapping the data sets and the operations to each other.

The control unit 120 may search for an operation corresponding to the combination of the plurality of data sets acquired from the signal transmitted from the ultrasound probe 200 in the storage unit 130. The control unit 120 may control the ultrasound diagnostic apparatus 100 to perform an operation identified by the searching.

Hereinafter, a method of operating the ultrasound diagnostic apparatus 100, according to an exemplary embodiment, will be described with reference to FIGS. 2 through 5.

Figure 2:
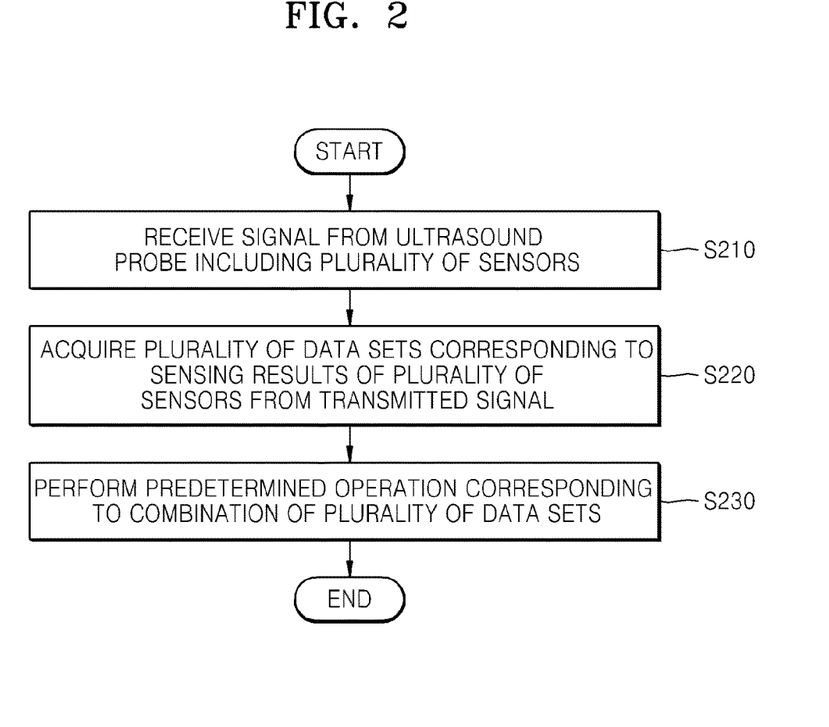
FIG. 2 is a flowchart of a method of operating an ultrasound diagnostic apparatus, according to an exemplary embodiment.

FIG. 2 is a flowchart of a method of operating the ultrasound diagnostic apparatus 100, according to an exemplary embodiment.

In operation S210, the ultrasound diagnostic apparatus 100 receives a signal from the ultrasound probe 200 including the first, second, and Nth sensors 201, 202, and 203. The signal transmitted from the ultrasound probe 200 may include a plurality of data sets corresponding to sensing results of the first, second, and Nth sensors 201, 202, and 203. Also, the signal transmitted from the ultrasound probe 200 may further include ultrasound image data of the object.

The first, second, and Nth sensors 201, 202, and 203 may include at least one of a touch sensor, a proximity sensor, a microphone, and a camera. However, exemplary embodiments are not limited thereto. Also, the ultrasound probe 200 may include a temperature sensor, an illuminance sensor, and a battery capacity check sensor of the ultrasound probe 200 as a sensor.

In operation S220, the ultrasound diagnostic apparatus 100 of the present exemplary embodiment acquires a plurality of data sets corresponding to the sensing results of the first, second, and Nth sensors 201, 202, and 203 from the transmitted signal.

According to an exemplary embodiment, the plurality of data sets may include information about times of acquiring the data sets by each of the first, second, and Nth sensors 201, 202, and 203. Therefore, the ultrasound diagnostic apparatus 100 may synchronize a plurality of data sets that are acquired at the same or similar times by the first, second, and Nth sensors 201, 202, and 203.

Figures 3A, 3B:
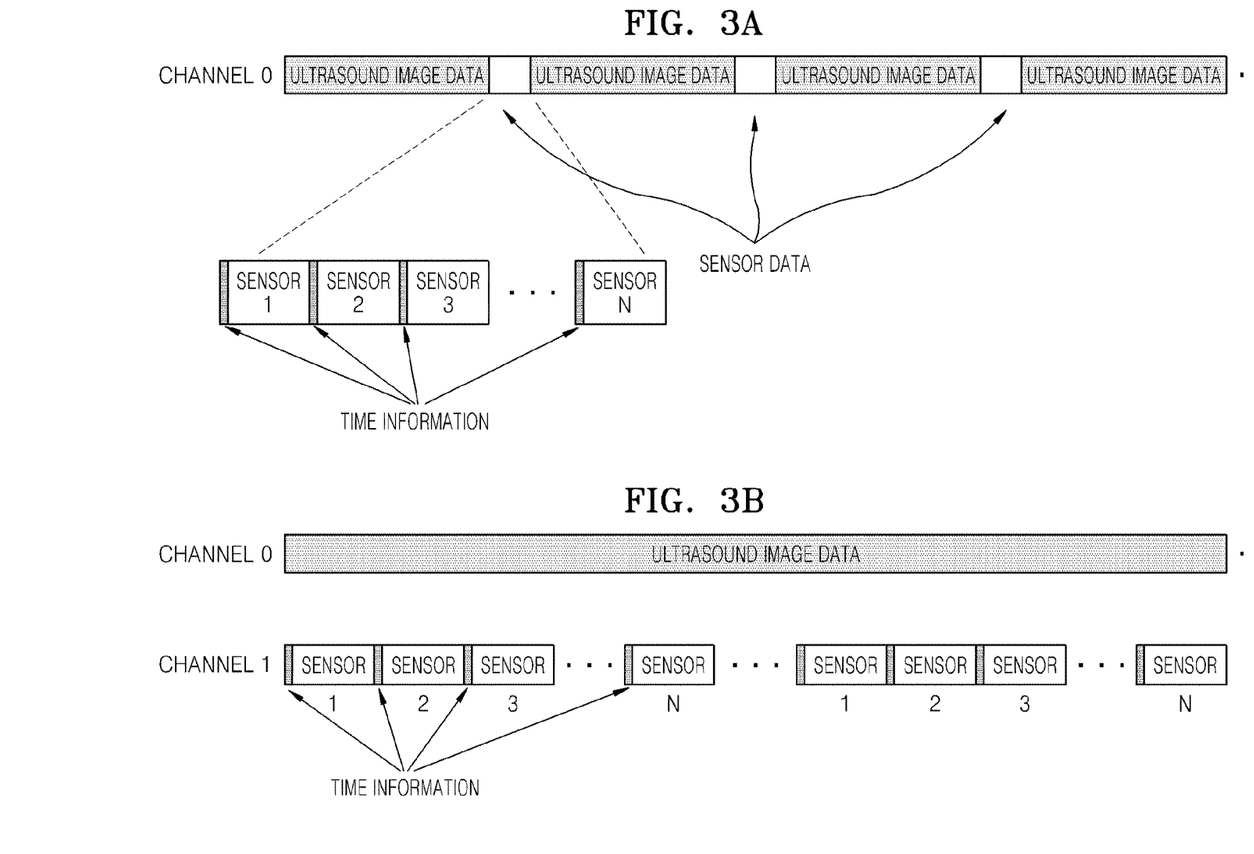
FIGS. 3A and 3B are diagrams illustrating signals transmitted from an ultrasound probe to an ultrasound diagnostic apparatus, according to an exemplary embodiment.

FIGS. 3A and 3B are diagrams illustrating signals transmitted from the ultrasound probe 200 to the ultrasound diagnostic apparatus 100, according to an exemplary embodiment.

As shown in FIG. 3A, the ultrasound probe 200 may transmit the plurality of data sets acquired by the plurality of sensors to the ultrasound diagnostic apparatus 100 with ultrasound image data in real-time. The ultrasound probe 200 may configure the plurality of data sets in additional packets to be distinguished from the ultrasound image data. According to an exemplary embodiment, the ultrasound diagnostic apparatus 100 may temporally synchronize the data sets acquired by the plurality of sensors by using the time information that is transmitted with the data sets acquired by the plurality of sensors.

Also, as shown in FIG. 3B, the ultrasound probe 200 may transmit the plurality of data sets acquired by the plurality of sensors and the ultrasound data via different wireless communication channels. The wireless communication channels are paths through which predetermined signals are transferred from the ultrasound probe 200 to the ultrasound diagnostic apparatus 100.

The ultrasound probe 200 may transmit the plurality of data sets and the ultrasound image data by using different wireless communication methods or by using signals of different frequency bands.

As shown in FIG. 3B, even when the plurality of data sets and the ultrasound image data are transferred via different wireless communication channels, the ultrasound probe 200 may transmit the information about the time of acquiring each data set to the ultrasound diagnostic apparatus 100 with the plurality of data sets acquired by the plurality of sensors.

In operation S230, the ultrasound diagnostic apparatus 100 may perform a predetermined operation corresponding to a combination of the plurality of data sets.

The ultrasound diagnostic apparatus 100 may perform a predetermined operation including at least one operation among operations of storing at least one of the plurality of data sets, displaying at least one of the plurality of data sets, and transmitting a control signal corresponding to the combination of the plurality of data sets to the ultrasound probe 200.

For example, the ultrasound diagnostic apparatus 100 may perform a predetermined operation corresponding to the combination of the plurality of data sets by classifying the information included in the plurality of data sets or searching for the operations that are stored in advance and which correspond to the plurality of data sets.

According to the present exemplary embodiment, the ultrasound diagnostic apparatus 100 may classify the plurality of data sets acquired from the ultrasound probe 200 as patient information, status information of the ultrasound probe 200, and information for controlling the ultrasound probe 200 based on the combination of the plurality of data sets.

The ultrasound diagnostic apparatus 100 may classify the plurality of data sets acquired by the ultrasound probe 200 as patient information based on the combination of the plurality of data sets. In this case, the ultrasound diagnostic apparatus 100 may store or display the data set acquired by at least one of the plurality of sensors as the patient information.

The ultrasound diagnostic apparatus 100 may classify the plurality of data sets acquired from the ultrasound probe 200 as status information of the ultrasound probe 200 based on the combination of the plurality of data sets. In this case, the ultrasound diagnostic apparatus 100 may store or display a location of the ultrasound probe 200, the remaining capacity of the battery, and a temperature of the ultrasound probe 200 as the status information of the ultrasound probe based on a data set acquired by at least one of the plurality of sensors.

The ultrasound probe 200 may transmit information about another device coupled to the ultrasound probe 200 to the ultrasound diagnostic apparatus 100. For example, the ultrasound diagnostic apparatus 100 may store or display a location of a needle used with the ultrasound probe 200 based on a data set acquired by at least one of the plurality of sensors.

Also, the ultrasound diagnostic apparatus 100 may classify the plurality of data sets acquired from the ultrasound probe 200 as information for controlling the ultrasound probe 200 based on the combination of the plurality of data sets. In this case, the ultrasound diagnostic apparatus 100 may generate a control signal corresponding to the combination of the plurality of data sets, and may transmit the generated control signal to the ultrasound probe 200.

According to another exemplary embodiment, the ultrasound diagnostic apparatus 100 may map the combinations of the plurality of data sets acquired by the first, second, and Nth sensors 201, 202, and 203 to the operations of the ultrasound diagnostic apparatus 100 in advance, and then, store the mapping results. The ultrasound diagnostic apparatus 100 may search for the operations that are mapped with the plurality of data sets and stored in advance, in order to perform the operation corresponding to the combination of the plurality of data sets.

The ultrasound diagnostic apparatus 100 may store or display at least one of the plurality of data sets based on search results. The ultrasound diagnostic apparatus 100 may further receive the ultrasound image data from the ultrasound probe 200. The ultrasound diagnostic apparatus 100 may store or display at least one of the plurality of data sets with the ultrasound image data, based on the combination of the plurality of data sets.

For example, the ultrasound diagnostic apparatus 100 may store or display at least one of a picture, a moving picture, and sound acquired according to a sensing result of at least one of the first, second, and Nth sensors 201, 202, and 203, based on the search result. Therefore, the user may, for example, store or display a picture of a patient with the ultrasound image data rapidly and conveniently. Also, the ultrasound diagnostic apparatus 100 may display status information of the ultrasound probe 200, for example, the remaining capacity of the battery and a temperature, acquired according to the sensing result of at least one of the plurality of sensors, namely, the first, second, . . . , and Nth sensors 201, 202, and 203, based on the combination of the plurality of data sets. Therefore, the user may acquire information about the status of the ultrasound probe 200 conveniently.

The ultrasound diagnostic apparatus 100 may transmit the control signal about the ultrasound probe 200 to the ultrasound probe 200 based on the search result. The control signal transmitted to the ultrasound probe 200 may be a signal controlling the ultrasound probe 200 to transmit and/or receive an ultrasound signal to and/or from the object and to acquire ultrasound image data of the object.

Figure 4:
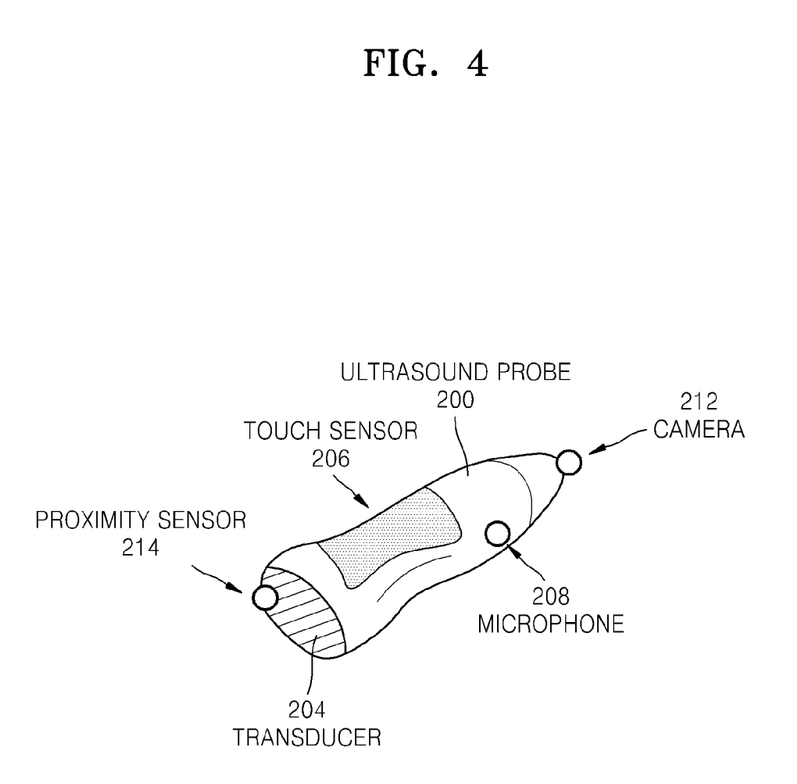
FIG. 4 is a diagram exemplarily showing an ultrasound probe including a plurality of sensors, according to an exemplary embodiment.

For convenience of understanding, an exemplary case where the ultrasound probe 200 includes a proximity sensor, a microphone, a touch sensor, and a camera, as shown in FIG. 4, will be described below. It is understood that the exemplary embodiments are not limited to this exemplary case.

FIG. 4 is a diagram of the ultrasound probe 200 including a plurality of sensors, according to an exemplary embodiment. As shown in FIG. 4, a proximity sensor 214 is disposed on a lower portion of the ultrasound probe 200. A transducer 204 which transmits an ultrasound signal to the object, a touch sensor 206 and a microphone 208 are disposed on side surfaces of the ultrasound probe 200, and a camera 212 may be disposed at an opposite side to the transducer 204.

However, exemplary embodiments are not limited thereto, and the ultrasound probe 200 according to an exemplary embodiment may include sensors other than the sensors shown in FIG. 4.

The ultrasound diagnostic apparatus 100 may sense whether the ultrasound probe 200 contacts the patient by using the proximity sensor 214, and then, may acquire a data set representing whether the user is currently scanning the patient.

The ultrasound diagnostic apparatus 100 may sense sound from the patient or the user by using the microphone 208, and may acquire a sound data set as the patient information. The ultrasound probe 200 may include a button for activating or deactivating the microphone 208 in order to sense sound for a predetermined period desired by the user. Also, the ultrasound probe 200 may acquire sound data set only when the sound is equal to or greater than a predetermined volume or is in a predetermined dB range as the patient information, in order to sense the sound within a predetermined time period desired by the user.

The ultrasound diagnostic apparatus 100 senses whether the user contacts the ultrasound probe 200 by using the touch sensor 206 to acquire information about whether the ultrasound probe 200 is in a usage state. The proximity sensor or the touch sensor may include an illuminance sensor for sensing light.

Also, the ultrasound diagnostic apparatus 100 may acquire data sets about gestures of the user's hand holding the ultrasound probe 200, by using the touch sensor 206.

Figure 5A:
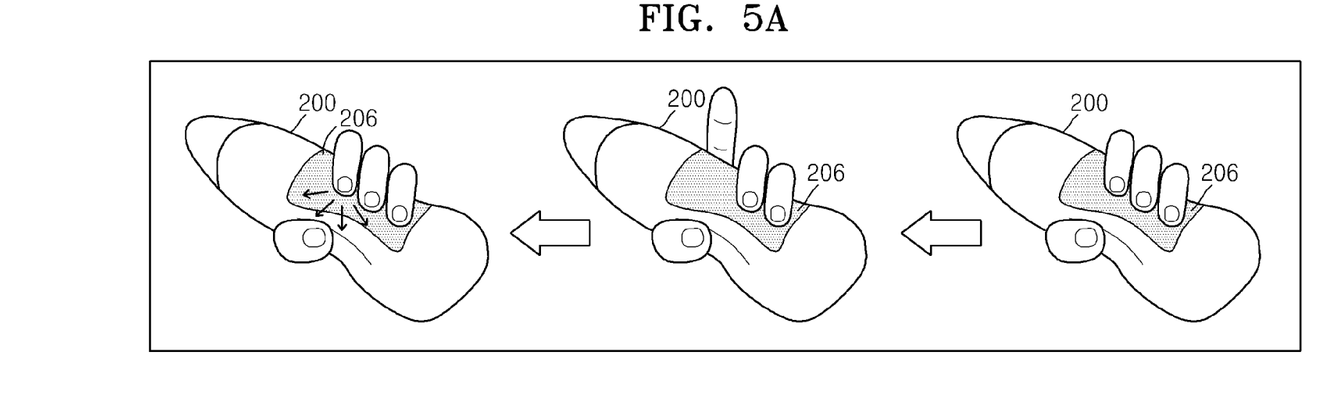
FIGS. 5A and 5B are diagrams illustrating data sets acquired according to sensing results of a touch sensor in an ultrasound probe, according to an exemplary embodiment.
Figure 5B:
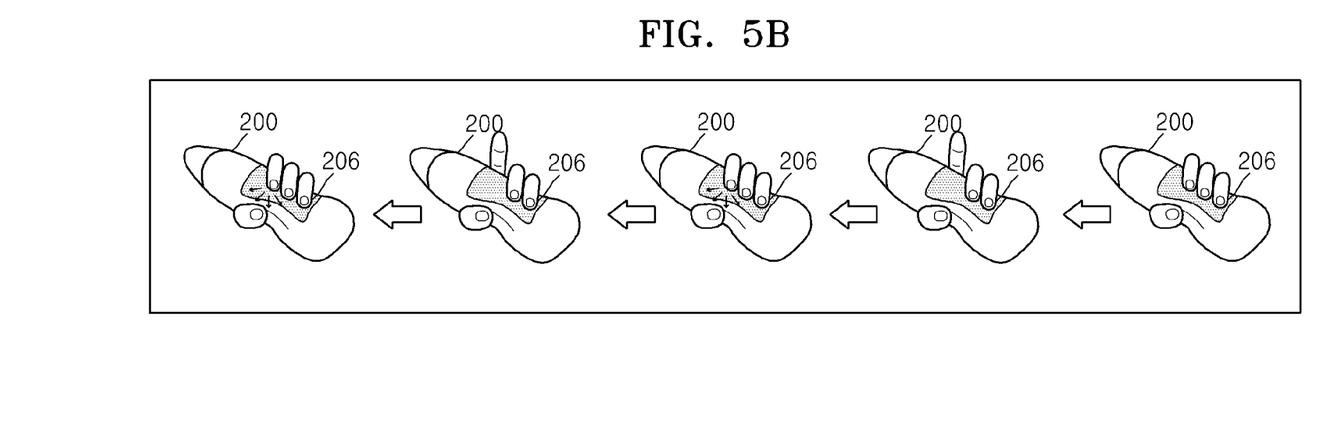

FIGS. 5A and 5B are diagrams illustrating the data sets acquired according to the sensing result of the touch sensor in the ultrasound probe 200, according to an exemplary embodiment.

For example, the ultrasound diagnostic apparatus 100 may determine a gesture of the user as shown in FIG. 5A to be "gesture 1". Specifically, if the ultrasound probe 200 senses five fingers of the user and then senses that an index finger of the user is detached and attached again, the ultrasound probe 200 may generate a data set indicating "gesture 1" according to the sensing result. The ultrasound probe 200 may transmit the data set indicating "gesture 1", which is acquired by the sensing result of the touch sensor 206, to the ultrasound diagnostic apparatus 100.

Also, the ultrasound diagnostic apparatus 100 may determine a gesture of the user shown in FIG. 5B to be "gesture 2". Specifically, if five fingers of the user are sensed, the second finger is not sensed and then sensed again, and within a predetermined time, the second finger is not sensed and then sensed again, the ultrasound probe 200 may generate a data set indicating "gesture 2" according to the sensing result. The ultrasound probe 200 may transmit the data set indicating "gesture 2", which is acquired according to the sensing result of the touch sensor 206, to the ultrasound diagnostic apparatus 100.

The ultrasound diagnostic apparatus 100 may acquire an image data set, that is, a picture, as the patient information, by using the camera 212. The ultrasound probe 200 may include a button for activating or deactivating the camera 212 in order to acquire the image data set for a predetermined time period desired by the user.

The ultrasound diagnostic apparatus 100 according to the present exemplary embodiment may perform predetermined operations corresponding to the combinations of the plurality of data sets acquired by the plurality of sensors.

As shown in the following table 1, the ultrasound diagnostic apparatus 100 may store the combinations of the plurality of data sets acquired by the plurality of sensors 201, 202 and 203 and the operations performed by the ultrasound diagnostic apparatus 100 after mapping the data sets and the operations with each other.

TABLE 1

| Proximity sensor | microphone | Touch sensor | camera | Operations to be performed | Content of performed operation |
|---|---|---|---|---|---|
| Scanning | OFF | gesture 1 | OFF | Transmit control signal | Freeze/unfreeze |
| No scan | OFF | gesture 1 | ON | Store patient information | Store image data |
| No scan | ON | gesture 2 | OFF | Store patient information | Store voice data |
| scanning | ON | gesture 2 | OFF | Transmit control signal | Control ultrasound probe based on voice data |

The ultrasound diagnostic apparatus 100 may acquire the plurality of data sets corresponding to the sensing results of the plurality of sensors, from the signal transmitted from the ultrasound probe 200.

The ultrasound diagnostic apparatus 100 may classify whether the plurality of data sets acquired from the ultrasound probe 200 will be used as the patient information or information for controlling the ultrasound probe 200, based on the combination of the plurality of data sets.

For example, a case where the ultrasound diagnostic apparatus 100 acquires a plurality of data sets including information [scanning, microphone off, gesture 1, camera off] from the signal transmitted from the ultrasound probe 200 is assumed. In this case, the ultrasound diagnostic apparatus 100 may determine that the plurality of data sets will be used as the information for controlling the ultrasound probe 200, based on the combination of the plurality of data sets. The ultrasound diagnostic apparatus 100 searches for the operation corresponding to the combination of the acquired plurality of data sets in Table 1, and may perform an operation identified by the searching. Referring to Table 1, the ultrasound diagnostic apparatus 100 may transmit a control signal to the ultrasound probe 200 so as to freeze or unfreeze the ultrasound probe 200. The operation of freezing or unfreezing the ultrasound probe 200 may denote stopping or restarting the operation of acquiring the ultrasound image data by transmitting and/or receiving the ultrasound signal to and/or from the object. In particular, when the five fingers of the user are all sensed by the touch sensor, the ultrasound diagnostic apparatus 100 determines that the user starts manipulation of the ultrasound probe 200, and then, may enable the ultrasound probe 200 to transmit and/or receive the ultrasound signal. In addition, when it is determined that the user's gesture is "gesture 1", the ultrasound diagnostic apparatus 100 stops the scanning operation of the ultrasound probe 200 so as to stop the operations of transmitting and/or receiving the ultrasound signal by the ultrasound probe 200.

As another example, when the ultrasound diagnostic apparatus 100 acquires a plurality of data sets including information [no scanning, microphone off, gesture 1, camera on] from the signal transmitted from the ultrasound probe 200, the ultrasound diagnostic apparatus 100 may store the picture acquired by using the camera as patient information based on the combination of the plurality of data sets.

As another example, when the ultrasound diagnostic apparatus 100 acquires a plurality of data sets including information [no scanning, microphone on, gesture 2, camera off] from the signal transmitted from the ultrasound probe 200, the ultrasound diagnostic apparatus 100 may store voice data acquired by using the microphone as the patient information based on the combination of the plurality of data sets. The voice data acquired by the microphone may include voice data of the user recording status of the patient and a diagnosis.

As another example, when the ultrasound diagnostic apparatus 100 acquires a plurality of data sets including information [scanning, microphone on, gesture 2, camera off] from the signal transmitted from the ultrasound probe 200, the ultrasound diagnostic apparatus 100 may determine that the plurality of data sets will be used as the information for controlling the ultrasound probe 200 based on the combination of the plurality of data sets. The ultrasound diagnostic apparatus 100 searches Table 1 for an operation corresponding to the combination of the plurality of data sets, and may perform an operation identified by the searching. Referring to Table 1, the ultrasound diagnostic apparatus 100 may transmit a control signal for controlling the ultrasound probe 200 based on the acquired voice data. For example, the ultrasound diagnostic apparatus 100 may determine the meaning of the voice command of the user by analyzing the voice data, and may transmit a control signal corresponding to the voice command of the user to the ultrasound probe 200.

Figure 6:
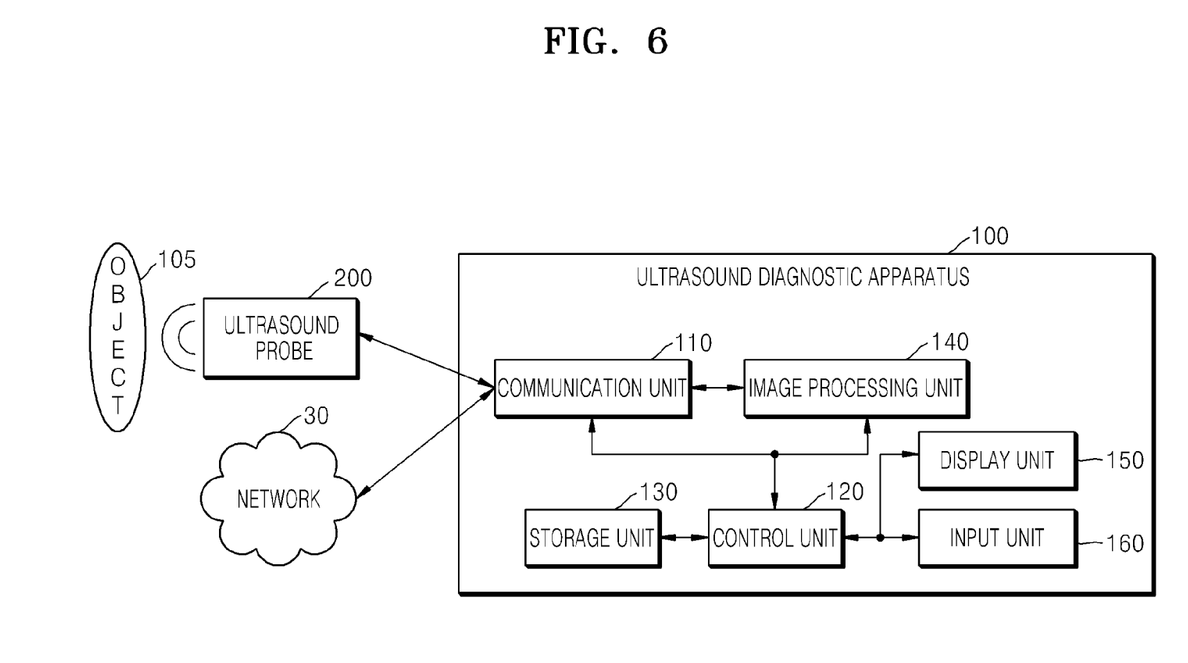
FIG. 6 is a block diagram of an ultrasound system to which the ultrasound probe and the ultrasound diagnostic apparatus according to an exemplary embodiment may be applied.

FIG. 6 is a block diagram of an ultrasound system to which the ultrasound probe 200 and the ultrasound diagnostic apparatus 100 according to an exemplary embodiment may be applied.

The ultrasound system of FIG. 6 may include the ultrasound diagnostic apparatus 100 and the ultrasound probe 200 according to an exemplary embodiment.

The ultrasound diagnostic apparatus 100 may include a communication unit 110, a control unit 120, a storage unit 130, an image processing unit 140, a display unit 150, and an input unit 160.

The ultrasound diagnostic apparatus 100 may be implemented as a portable type, as well as a cart type. A portable type ultrasound diagnostic apparatus may include a picture archiving and communication system (PACS) viewer, a hand-carried cardiac ultrasound (HCU) device, a smartphone, a laptop computer, a personal digital assistant (PDA), a tablet PC, or the like.

The communication unit 110 may perform wired or wireless communication with the ultrasound probe 200. The communication unit 110 may transmit a control signal provided from the control unit 120 to the ultrasound probe 200, and may receive ultrasound image data transmitted from the ultrasound probe 200.

Also, the communication unit 110 may be connected to a network 30 via wires or wirelessly to communicate with an external device or a server. The communication unit 110 may transmit and/or receive data to and/or from a hospital server or other medical devices in the hospital through a PACS system. Also, the communication unit 110 may perform data communication according to a digital imaging and communications in medicine (DICOM) standard.

The communication unit 110 may transmit and/or receive data relating to the diagnosis of the object, such as ultrasound images, ultrasound data, or Doppler data of the object, via the network 30, and may receive medical images captured by other medical apparatuses, such as a computed tomography (CT) apparatus, a magnetic resonance imaging (MRI) apparatus, or an X-ray apparatus. Moreover, the communication unit 110 may receive information about a medical history or a treatment schedule of the patient from the server to use the information to diagnose the object. In addition, the communication unit 110 may perform data communication with a portable device of a doctor or a patient, as well as the server or the medical apparatus in the hospital.

A short distance communication technology used by the communication unit 110 may include a wireless LAN (WLAN), Wi-Fi, Bluetooth, Zigbee, Wi-Fi direct (WFD), ultra wideband (UWB), infrared data association (IrDA), Bluetooth low energy (BLE), near field communication (NFC), or the like, but is not limited thereto.

Also, a wired communication technology that the communication unit 110 may use may include a pair cable, a coaxial cable, an optical fiber cable, Ethernet cable, or the like.

The communication unit 110 may use a mobile communication technology to transmit and/or receive wireless signals to and/or from at least one of a base station, an external terminal, and a server on a mobile communication network. According to an exemplary embodiment, a wireless signal may include a voice signal, a video call signal, or other various types of data according to text and/or multimedia transmission, as well as other types of transmissions.

The control unit 120 may control overall operations of the ultrasound diagnostic apparatus 100. That is, the control unit 120 may control operations of the ultrasound probe 200, the communication unit 110, the storage unit 130, the image processing unit 140, the display unit 150, and the input unit 160 shown in FIG. 6.

The storage unit 130 stores various types of information processed by the ultrasound diagnostic apparatus 100. For example, the storage unit 130 may store medical data related to the diagnosis of the object such as input/output ultrasound data, ultrasound images, and the like, and may store algorithms or programs executed in the ultrasound diagnostic apparatus 100.

The storage unit 130 may be implemented as various kinds of storage media such as a flash memory, a hard disk, and electrically erasable and programmable read only memory (EEPROM). Also, the ultrasound diagnostic apparatus 100 may manage a web storage or a cloud server configured to perform a storage function of the storage unit 130 on the web.

The image processing unit 140 may generate and display an ultrasound image through a scan conversion of the ultrasound image data transmitted from the ultrasound probe 200 via the communication unit 110. In addition, the ultrasound image may be a grayscale ultrasound image obtained by scanning the object according to an amplitude (A) mode, a brightness (B) mode, and a motion (M) mode, and a Doppler image showing movement of the object. The Doppler image may include a blood flow image (or a color Doppler image) representing blood flow, a tissue Doppler image representing movement of tissue, and a spectral Doppler image representing a moving velocity of the object as a waveform.

The display unit 150 displays and outputs the generated ultrasound image. The display unit 150 may display various types of information processed by the ultrasound diagnostic apparatus 100, as well as the ultrasound image itself, on a screen as a graphical user interface (GUI). The ultrasound diagnostic apparatus 100 may include two or more display units 150.

The input unit 160 is a unit for receiving data input for controlling the ultrasound diagnostic apparatus 100 from the user. The input unit 160 may include hardware configurations such as a keypad, a mouse, a touch panel, a touch screen, a trackball, and a jog switch, but is not limited thereto. That is, the input unit 160 may include various types of input units such as an electrocardiogram (ECG) measuring module, a respiratory measuring module, a voice recognition sensor, a gesture recognition sensor, a fingerprint recognition sensor, an iris recognition sensor, a depth sensor, a distance sensor, and the like.

Some or all of the ultrasound probe 200, the communication unit 110, the control unit 120, the storage unit 130, the image processing unit 140, the display unit 150, and the input unit 160 may be implemented by software modules; however, exemplary embodiments are not limited thereto, and, some of the above components may be implemented by hardware. Also, at least some of the communication unit 110, the storage unit 130, and the image processing unit 140 may be included in the control unit 120; however, exemplary embodiments are not limited thereto. Also, at least some of the communication unit 110, the control unit 120, the storage unit 130, and the image processing unit 140 may be included in the ultrasound probe 200; however, exemplary embodiments are not limited thereto.

The ultrasound probe 200 may transmit an ultrasound signal to an object 105 according to a control signal transmitted from the ultrasound diagnostic apparatus 100, and may receive an echo signal reflected by the object 105. The ultrasound probe 200 includes a plurality of transducers that vibrate according to an electric signal to generate ultrasonic waves having acoustic energy.

The ultrasound probe 200 generates pulses for forming a transmission ultrasonic wave according to a predetermined pulse repetition frequency (PRF) through the control signal transmitted from the ultrasound diagnostic apparatus 100. The ultrasound probe 200 applies a delay time for determining transmission directionality to the pulses. Each of the pulses, to which the delay time is applied, corresponds to each piezoelectric vibrator included in the transducers. The ultrasound probe 200 applies the pulses corresponding to the plurality of piezoelectric vibrators at timings corresponding to the pulses to which the delay time is applied.

The ultrasound probe 200 may generate the ultrasound image data by processing the echo signals reflected from the object 105. The ultrasound probe 200 may amplify the echo signals with respect to each channel, and perform an analog-digital conversion on the amplified echo signals. The ultrasound probe 200 applies the delay time for determining reception directionality to the echo signals that are converted to digital signals, and then, the ultrasound probe 200 may add the echo signals to which the delay time is applied together to generate ultrasound image data.

As described above, the ultrasound diagnostic apparatus 100 according to exemplary embodiments may acquire the control command of the user from the sensing results of the plurality of sensors included in the ultrasound probe 200, and thus, the user may easily control the ultrasound system. In addition, the ultrasound diagnostic apparatus 100 according to an exemplary embodiment may store the sensing results of the plurality of sensors as patient information with the ultrasound image data of the patient. Also, the ultrasound diagnostic apparatus 100 may acquire the sensing results of the plurality of sensors as the status information of the ultrasound probe 200 and may display the status information of the ultrasound probe 200, and thus, the user may monitor the status of the ultrasound probe 200 in real-time.

The exemplary embodiments can be implemented as digital electronic circuits, computer software, firmware, hardware including structures disclosed in the present specification or equivalent structures thereof, or a combination thereof. The computer-readable recording medium is any available medium accessible by the computer, volatile and non-volatile media, and isolation and non-isolation type media. Also, the computer-readable recording medium may include computer storage media and communication media. The computer storage media include volatile and non-volatile and isolation or non-isolation type media embodied by a certain method or technology for storing computer-readable commands, data structure, program modules, or other data. The communication media typically include computer-readable commands, data structure, program modules, or modulated data signals, or other transferring mechanisms, and may include any information transfer medium.

While the exemplary embodiments have been particularly shown and described with reference to certain exemplary embodiments thereof, it will be understood by those skilled in the art that various changes in form and details may be made therein without departing from the spirit and scope of the exemplary embodiments as defined by the appended claims. The exemplary embodiments should be considered in a descriptive sense only and not for purposes of limitation. Therefore, the scope of the exemplary embodiments is defined not by the detailed description but by the appended claims, and all differences within the scope will be construed as being included in the exemplary embodiments.

What is claimed is:

1. An ultrasound diagnostic apparatus comprising:
   a communicator comprising one of an antenna or a cable and configured to receive, using the one of the antenna or the cable, a signal from an ultrasound probe comprising a plurality of sensors, the ultrasound probe being external to the ultrasound diagnostic apparatus;
   a controller comprising an electronic circuit configured to acquire a plurality of data sets corresponding to sensing results of the plurality of sensors from the signal, and perform a predetermined operation corresponding to a combination of the plurality of data sets; and
   a storage configured to store information mapping a plurality of combinations of data sets from among the plurality of data sets to a plurality of operations of the ultrasound diagnostic apparatus, respectively, the plurality of combinations of data sets being different from each other and the plurality of operations of the ultrasound diagnostic apparatus being different from each other,
   wherein the plurality of data sets comprises information configured to synchronize timings when the plurality of data sets is acquired by the plurality of sensors, and
   wherein the predetermined operation includes transmitting a control signal corresponding to the combination of the plurality of data sets to the ultrasound probe,
   wherein the plurality of sensors comprises:
   a transducer configured to transmit an ultrasound signal; and
   at least one sensor other than the transducer, the at least one sensor being a type of sensor different from the transducer and being configured to transmit a signal of a type different from the ultrasound signal.

2. The ultrasound diagnostic apparatus of claim 1, wherein the predetermined operation further includes at least one operation among operations of storing at least one data set of the plurality of data sets and displaying at least one data set of the plurality of data sets.

3. The ultrasound diagnostic apparatus of claim 1,
   wherein the controller is configured to search the plurality of operations stored in the storage for the predetermined operation corresponding to the combination of the plurality of data sets.

4. The ultrasound diagnostic apparatus of claim 1, wherein the controller is configured to control the ultrasound diagnostic apparatus to store or display at least one of an acquired picture, a moving picture, and sound according to a sensing result of at least one of the plurality of sensors, based on the combination of the plurality of data sets.

5. The ultrasound diagnostic apparatus of claim 1, wherein the control signal is configured to control the ultrasound probe to acquire ultrasound image data of an object by transmitting or receiving an ultrasound signal to or from the object, based on the combination of the plurality of data sets.

6. The ultrasound diagnostic apparatus of claim 1, wherein the signal comprises ultrasound image data of an object, and the controller is configured to control the ultrasound diagnostic apparatus to store or display at least one data set of the plurality of data sets as information about the object with the ultrasound image data, based on the combination of the plurality of data sets.

7. The ultrasound diagnostic apparatus of claim 1, wherein the plurality of sensors further comprise at least one of a touch sensor, a proximity sensor, a microphone, and a camera.

8. A method of operating an ultrasound diagnostic apparatus, the method comprising:
receiving a signal from an ultrasound probe including a plurality of sensors, the ultrasound probe being external to the ultrasound diagnostic apparatus;
acquiring a plurality of data sets corresponding to sensing results of the plurality of sensors from the signal;
performing a predetermined operation corresponding to a combination of the plurality of data sets, and
storing information mapping a plurality of combinations of data sets from among the plurality of data sets to a plurality of operations of the ultrasound diagnostic apparatus, respectively, the plurality of combinations of data sets being different from each other and the plurality of operations of the ultrasound diagnostic apparatus being different from each other,
wherein the plurality of data sets comprises information configured to synchronize timings when the plurality of data sets is acquired by the plurality of sensors, and
wherein the performing of the predetermined operation comprises transmitting a control signal corresponding to the combination of the plurality of data sets to the ultrasound probe,
wherein the plurality of sensors includes a transducer configured to transmit an ultrasound signal and at least one sensor other than the transducer, the at least one sensor being a type of sensor different from the transducer and being configured to transmit a signal of a type different from the ultrasound signal.

9. The method of claim 8, wherein the performing of the predetermined operation further comprises performing at least one of storing at least one of the plurality of data sets and displaying at least one of the plurality of data sets.

10. The method of claim 8,
wherein the performing of the predetermined operation further comprises searching the plurality of operations for the predetermined operation corresponding to the combination of the plurality of data sets.

11. The method of claim 8, wherein the performing of the predetermined operation further comprises storing or displaying at least one of an acquired picture, a moving picture, and sound according to a sensing result of at least one of the plurality of sensors, based on the combination of the plurality of data sets.

12. The method of claim 8, wherein the control signal is configured to control the ultrasound probe to acquire ultrasound image data of an object by transmitting or receiving an ultrasound signal to or from the object, based on the combination of the plurality of data sets.

13. The method of claim 8, wherein the signal further comprises ultrasound image data of an object, and the performing of the predetermined operation further comprises storing or displaying at least one data set of the plurality of data sets as information about the object with the ultrasound image data, based on the combination of the plurality of data sets.

14. The method of claim 8, wherein the plurality of sensors includes at least one of a touch sensor, a proximity sensor, a microphone, and a camera.

15. A non-transitory computer-readable recording medium having embodied thereon a program for executing a method of operating an ultrasound diagnostic apparatus in a computer, wherein the method comprises:
receiving a signal from an ultrasound probe including a plurality of sensors, the ultrasound probe being external to the ultrasound diagnostic apparatus;
acquiring a plurality of data sets corresponding to sensing results of the plurality of sensors from the signal;
performing a predetermined operation corresponding to a combination of the plurality of data sets; and
storing information mapping a plurality of combinations of data sets from among the plurality of data sets to a plurality of operations of the ultrasound diagnostic apparatus, respectively, the plurality of combinations of data sets being different from each other and the plurality of operations of the ultrasound diagnostic apparatus being different from each other,
wherein the plurality of data sets comprises information configured to synchronize timings when the plurality of data sets is acquired by the plurality of sensors, and
wherein the performing of the predetermined operation comprises transmitting a control signal corresponding to the combination of the plurality of data sets to the ultrasound probe,
wherein the plurality of sensors includes a transducer configured to transmit an ultrasound signal and at least one sensor other than the transducer, the at least one sensor being a type of sensor different from the transducer and being configured to transmit a signal of a type different from the ultrasound signal.

* * * * *